United States Patent [19]

Vandenberg

[11] Patent Number: Plant 6,497

[45] Date of Patent: Dec. 27, 1988

[54] CHRYSANTHEMUM PLANT NAMED BRIOSO

[75] Inventor: Cornelis P. Vandenberg, Salinas, Calif.

[73] Assignee: Yoder Brothers, Inc., Barberton, Ohio

[21] Appl. No.: 49,779

[22] Filed: May 14, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Brioso particularly characterized as to uniqueness by the combined characteristics of flat capitulum form; daisy capitulum type; purple ray floret color; diameter across face of capitulum of up to 125 mm at maturity; uniform nine week photoperiodic flowering response to short days; tall plant height when grown single stem; 10 to 25 cm peduncles on open, normally terminal sprays; and 13 degrees Celsius minimum temperature tolerance for initiation and development of flowering buds with a 12 to 13 hour continuous dark period.

3 Drawing Sheets

The present invention comprises a new and distinct cultivar of Chrysanthemum, botanically known as *Chrysanthemum morifolium* Ramat., and referred to by the cultivar name Brioso.

Brioso, identified as 83678009, was originated from a cross made in a controlled breeding program in Salinas, Calif., in 1982.

The female parent of Brioso was the cultivar identified as White Nova, disclosed in U.S. Plant Pat. No. 5,289. The male parent of Brioso, identified as 80613001, was an unnamed seedling.

Brioso was discovered and selected as one flowering plant within the progeny of the stated cross by Cornelis P. VandenBerg in November 1983, in a controlled enviroment in Salinas, Calif.

The first act of asexual reproduction of Brioso was accomplished when vegetative cuttings were taken from the initial selection in January 1984 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Brioso are firmly fixed and are retained through successive generations of asexual reproduction.

Brioso has not been observed under all possible environmental conditions. The phenotype may vary significantly with variations in environment such as temperature, light intensity and daylength.

The following observations, measurements and comparisons describe plants grown in Salinas, Calif., and Leamington, Canada, under greenhouse conditions which approximate those generally used in commercial greenhouse practice.

The following traits have been repeatedly observed and are determined to be basic characteristics of Brioso, which, in combination, distinguish this Chrysanthemum as a new and distinct cultivar:

1. Flat capitulum form.
2. Daisy capitulum type.
3. Purple ray floret color.
4. Diameter across face of capitulum up to 125 mm at maturity.

5. Uniform nine week photoperiodic flowering response to short days.
6. Peduncle length ranging from 10 to 25 cm.
7. Tall plant height, requiring one long day week prior to short days to attain a flowered plant height of 100 to 110 cm for year-round flowerings.
8. Low temperature tolerance of 13 degrees Celsius for initiation and development when grown in single stem cut spray programs with a continuous dark period of 12 to 13 hours.

The accompanying photographic drawings show typical inflorescence and leaf characteristics of Brioso, with the colors being as nearly true as possible with illustrations of this type. Sheet 1 is a color photograph of Brioso grown as a single stem cut spray. Sheet 2 is a black and white photograph of three views of the inflorescence of Brioso. Sheet 3 is a black and white photograph showing the upper and under sides of the leaves of Brioso at three stages of development (mature, intermediate and immature).

Of the commercial cultivars known to the inventor, the most similar in comparison to Brioso is Blue Marble (unpatented). Reference is made to attached Chart A, which compares certain characteristics of Brioso to the same characteristics of Blue Marble.

Similar traits are capitulum form and type, flowering response and low temperature tolerance. Brioso has a wider spray formation, a larger diameter of capitulum and a taller plant height than Blue Marble. Under adverse conditions Blue Marble exhibits compounding of the spray formation and develops bract tissue in the disc. The spray formation of Brioso is always terminal, with no development of bracts.

In the following description color references are made to The Royal Horticultural Society Colour Chart. The color values were determined on plant material grown in Salinas, Calif. on Oct. 17, 1986.

Classification:

*Botanical.*—*Chrysanthemum morifolium,* Ramat., cv. Brioso.

*Commercial.*—Daisy cut spray mum.

INFLORESCENCE

A. Capitulum:

*Form.*—Flat.

*Type.*—Daisy.

*Diameter across face.*—Up to 125 mm at maturity.

B. Corolla of ray florets:

*Color (general tonality from a distance of three meters).*—Purple.

*Color (upper surface).*—Between 74D and 78C-D.

*Color (under surface).*—78D.

*Shape.*—Oblong.

C. Corolla of disc florets:

*Color (mature).*—14A.

*Color (immature).*—144B.

D. Reproductive organs:

*Androecium.*—Present on disc florets only; scant pollen.

*Gynoecium.*—Present on both ray and disc florets.

PLANT

A. General appearance:

*Height.*—Tall; 100 to 110 cm as a flowering plant from rooted cutting with seven long days for year-round flowerings maintaining a continuous dark period of 12 to 13 hours.

B. Foliage:

*Color (upper surface).*—147A.

*Color (under surface).*—147B.

*Shape.*—Lobed and slightly serrated.

CHART A

COMPARISON OF BRIOSO AND BLUE MARBLE

| CULTIVAR | RAY FLORET COLOR | CAPITULUM FORM & TYPE | BRANCHING PATTERN |
|---|---|---|---|
| BRIOSO | PURPLE | FLAT DAISY | WIDE, TERMINAL 10 to 25 cm PEDUNCLES |
| BLUE MARBLE | LAVENDER PINK | FLAT DAISY | UPRIGHT, TERMINAL to COMPOUND 20 to 25 cm PEDUNCLES |

| DIAMETER ACROSS FACE OF CAPITULUM | PLANT HEIGHT | FLOWERING RESPONSE PERIOD | TOLERANCE OF 13° C. |
|---|---|---|---|
| UP TO 125 mm | TALL | 9 WEEKS | GOOD |
| UP TO 9 cm | MEDIUM | 9 WEEKS | GOOD |

COMPARISONS MADE OF PLANTS GROWN AS SINGLE STEM SPRAY CUT MUMS IN SALINAS, CALIFORNIA AND IN LEAMINGTON, CANADA

I claim:

1. A new and distinct plant of Chrysanthemum named Brioso, as described and illustrated, and particularly characterized as to uniqueness by the combined characteristics of flat capitulum form; daisy capitulum type; purple ray floret color; diameter across face of capitulum of up to 125 mm at maturity; uniform nine week photoperiodic flowering response to short days; tall plant height when grown single stem; 10 to 25 cm peduncles on open, normally terminal sprays; and 13 degrees Celsium minimum temperature tolerance for initiation and development of flowering buds.

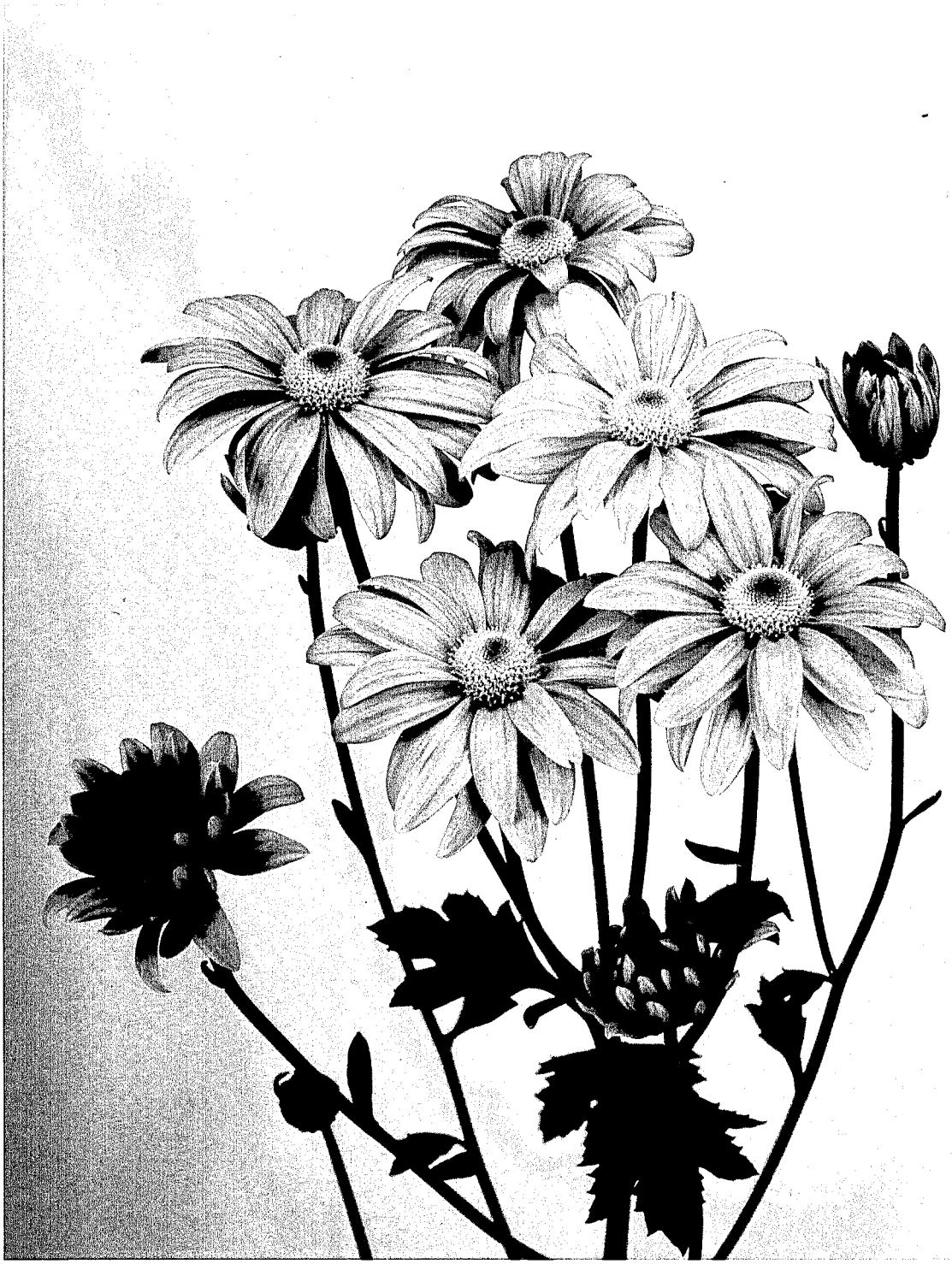

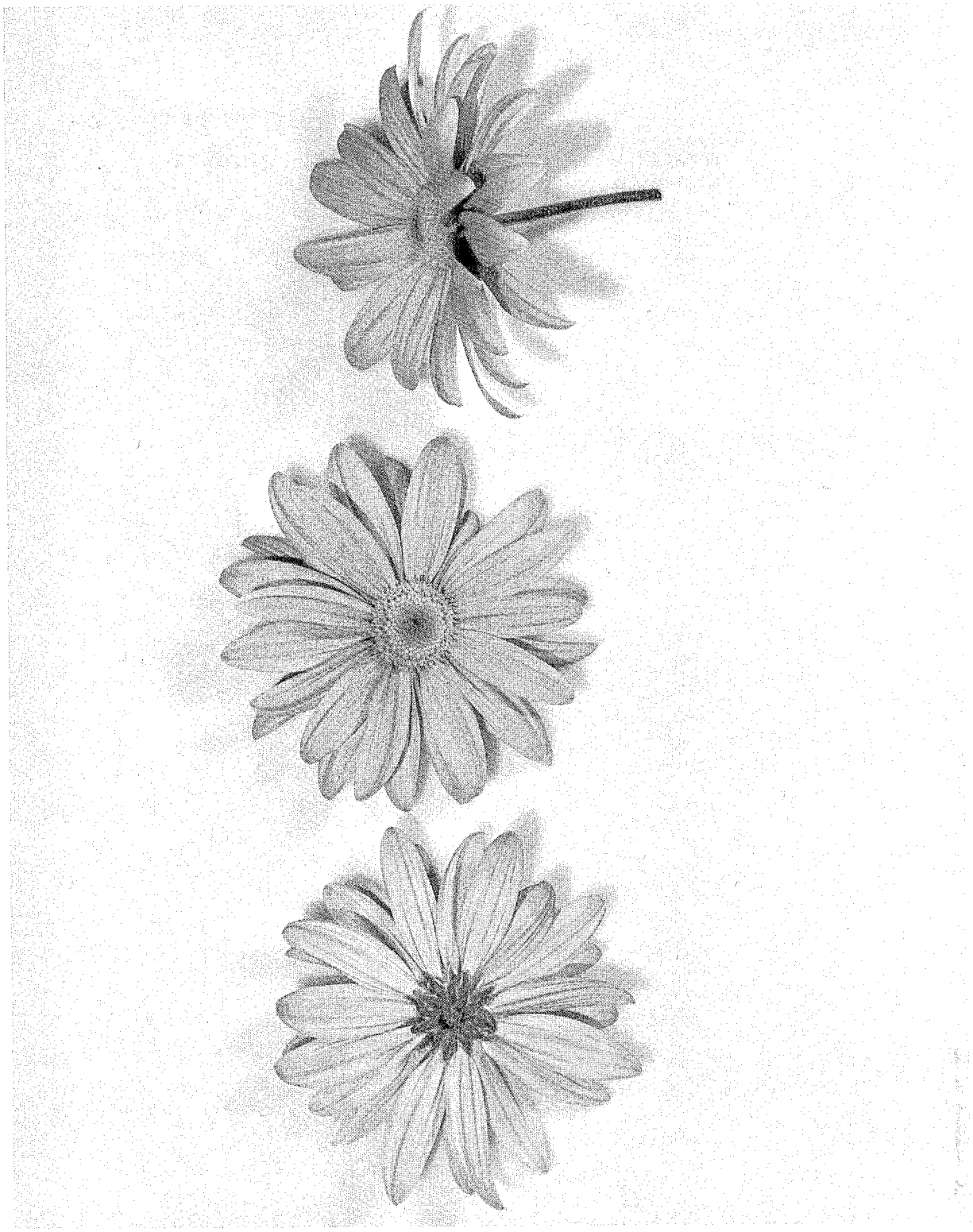

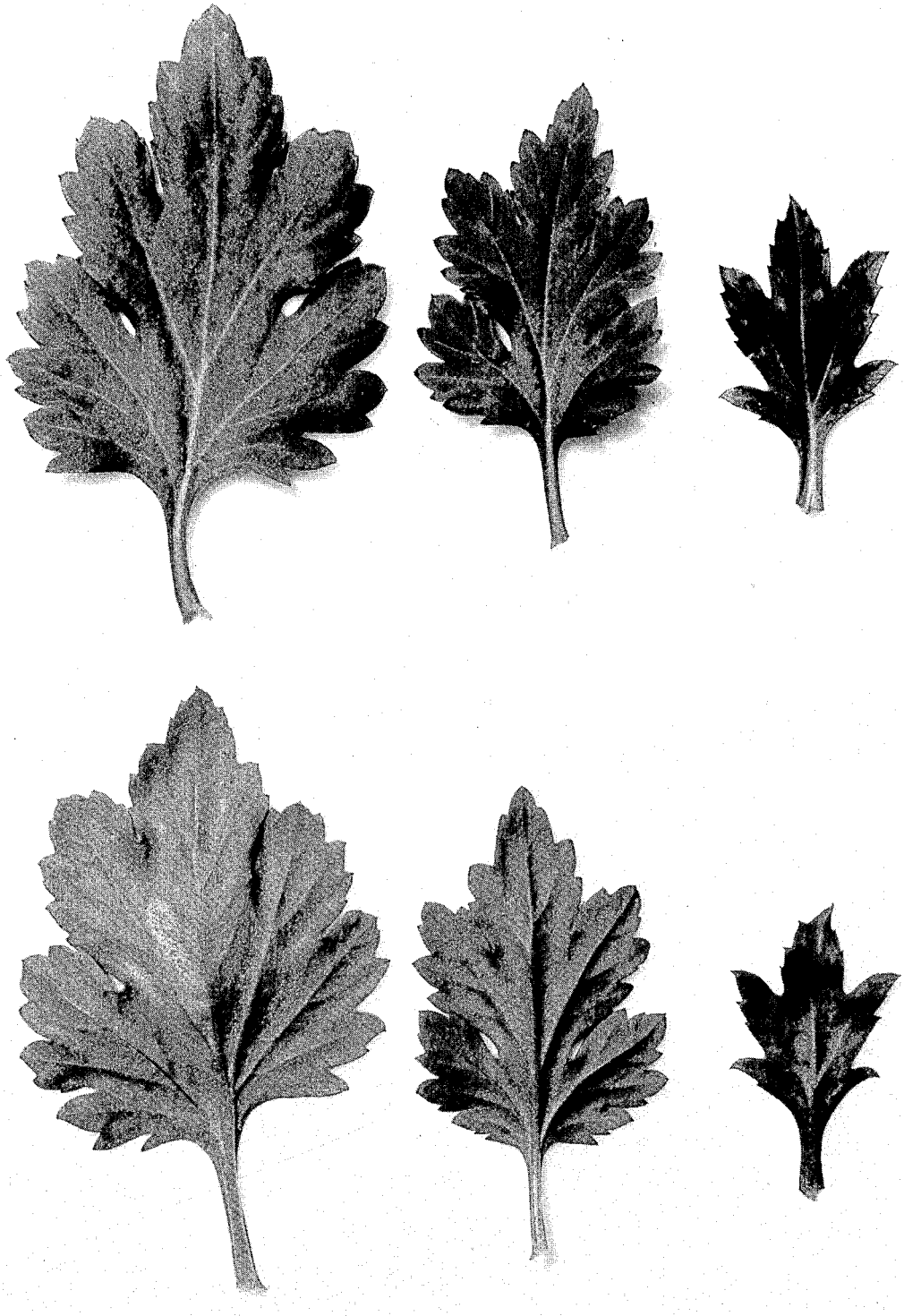

* * * * *